United States Patent

Hageman

[11] Patent Number: 6,011,011
[45] Date of Patent: Jan. 4, 2000

[54] SUSTAINED-RELEASE PROTEIN FORMULATIONS

[75] Inventor: Michael J. Hageman, Kalamazoo, Mich.

[73] Assignee: Pharmacia & Upjohn Company, Kalamazoo, Mich.

[21] Appl. No.: 08/407,327

[22] Filed: Mar. 20, 1995

Related U.S. Application Data

[63] Continuation of application No. PCT/US93/07756, Aug. 23, 1993, which is a continuation-in-part of application No. 07/963,365, Oct. 20, 1992, abandoned, and a continuation-in-part of application No. 07/947,872, Sep. 21, 1992, abandoned.

[51] Int. Cl.[7] .......................... A61K 38/27; A61K 38/25
[52] U.S. Cl. .................................. 514/12; 514/14; 514/21; 424/438
[58] Field of Search .................................. 514/12, 21, 14; 424/438

[56] References Cited

U.S. PATENT DOCUMENTS

| | | | |
|---|---|---|---|
| 3,966,962 | 6/1976 | Yalkowsky | 424/305 |
| 4,041,155 | 8/1977 | Fenichel et al. | 424/177 |
| 4,301,175 | 11/1981 | Yalkowsky | 424/305 |
| 4,680,312 | 7/1987 | Johnson | 514/573 |
| 4,795,641 | 1/1989 | Kashdan | 424/457 |
| 4,832,967 | 5/1989 | Autant et al. | 426/303 |
| 4,859,696 | 8/1989 | Kamiya et al. | 424/45 |
| 4,917,685 | 4/1990 | Viswanathan et al. | 604/891.1 |
| 4,977,140 | 12/1990 | Ferguson et al. | 514/12 |
| 4,983,385 | 1/1991 | Hasegawa et al. | 514/772.4 |
| 5,004,728 | 4/1991 | Chalupa et al. | 514/560 |
| 5,013,713 | 5/1991 | Mitchell | 514/2 |
| 5,091,185 | 2/1992 | Castillo et al. | 424/438 |
| 5,171,580 | 12/1992 | Iamartino et al. | 424/490 |
| 5,179,189 | 1/1993 | Domb et al. | 528/271 |
| 5,206,219 | 4/1993 | Desai | 514/3 |

FOREIGN PATENT DOCUMENTS

| | | | |
|---|---|---|---|
| 0 140 255 | 5/1985 | European Pat. Off. | A61K 9/00 |
| 0398287 | 5/1990 | European Pat. Off. | A61K 9/08 |
| 0 413 538 | 2/1991 | European Pat. Off. | A61K 31/71 |
| 1185340 | 3/1970 | United Kingdom . | |
| 91 16929 | 11/1991 | WIPO | A61K 47/10 |

OTHER PUBLICATIONS

The Merck Index, 11th Edition, p. 1204.

*Primary Examiner*—Chhaya D. Sayala
*Attorney, Agent, or Firm*—James D. Darnley, Jr.; Greg Steele

[57] ABSTRACT

The invention provides novel compositions useful for the sustained-release of bioactive proteins. More particularly, the present invention relates to novel suspensions of somatotropin and growth hormone releasing factor, in triacetin or polyethylene glycol. Also provided are methods of using these novel compositions as vehicles for the sustained or prolonged release of the bioactive protein or peptide.

36 Claims, No Drawings

SUSTAINED-RELEASE PROTEIN FORMULATIONS

CROSS-REFERENCE TO RELATED APPLICATIONS

This application is a continuation of International Patent Application No. PCT/US93/07756, filed Aug. 23, 1993, which is a continuation-in-part of U.S. Ser. No.07/963,365, filed Oct. 20, 1992, abandoned, and of U.S. Ser. No. 07/947,872, filed Sep. 21, 1992, abandoned.

FIELD OF THE INVENTION

The present invention relates to novel compositions useful for the sustained-release of bioactive proteins. More particularly, the present invention relates to novel suspensions of a protein, more particularly somatotropins and growth hormone releasing factor, in triacetin and in polyethylene glycols. Also provided are methods of using these novel compositions for the sustained or prolonged release of the bioactive proteins.

BACKGROUND OF THE INVENTION

With the advent of genetic engineering, the large-scale availability of many bioactive peptides and proteins has been achieved. However, the administration of these recombinantly produced peptides and proteins presents a unique set of problems. In many cases the maintenance of the biological effect of these proteins requires long-term administration. Daily administration of these agents in aqueous vehicles is inconvenient and costly; sustained or prolonged release is preferred. In addition, proteins are highly unstable in an aqueous environment most suitable for administration.

For instance, bovine somatotropin (bSt) is being produced by recombinant DNA technology. It is well recognized that lactating dairy cows administered recombinant bSt (rbSt) produce more milk compared with controls. Administration of rbSt in a sustained release vehicle will allow less frequent dosing which would be expected to result in a savings of time and labor to dairymen.

Biocompatible oils have long been used as vehicles to provide sustained delivery of many drugs, including proteins and specifically somatotropins. Oleaginous vehicles also have the practical advantage of providing a low water content environment to the suspended, dehydrated protein, thus providing sufficient stability for long term storage of a ready-to-inject product.

An alternative approach to stabilization involves the use of a non-aqueous, water miscible vehicle. Numerous such vehicles are known, e.g., propylene glycol, glycerin, dimethyl sulfoxide (DMSO), the polyethylene glycols, triacetin, n-methylpyrrolidone, 2-pyrrolidone, and N,N-dimethylacetamide. However, at protein concentrations needed for an extended release product, these vehicles typically either do not form a suspension or, when mixture is possible, form a suspension not suitable for a commercial product. I have found an exception to these formulation difficulties in glyceryl triacetate (triacetin) and in the polyethylene glycols (PEG).

Triacetin is a well known article of commerce which is used primarily in industrial applications. A number of pharmaceutical uses have been reported, e.g., as a solvent for preparing stable solution formulations of prostaglandin-like compounds (U.S. Pat. Nos. 3,966,962, 4,301,175, and 4,680,312), as an antifungal agent (U.S. Pat. No. 3,070,497), as a solvent in tetracycline solutions (U.S. Pat. No. 3,219,529), as a solvent in various topical formulations (GB 2150830, JP 63130541, and JP 59044311 (as a plasticizer in polymeric drug delivery systems); U.S. Pat. No. 4,857,313 (as a co-polymer for transdermal delivery systems), and as a dispersing agent in the food industry for hydrophilic colloids such as gelatin (GB 1185340). Triacetin is included in the GRAS (generally regarded as safe) list compiled by the U.S. Food and Drug Administration. The Merck Index, 10th Edition, reports triacetin is soluble in water to the extent of about one part triacetin to 14 parts water.

The polyethylene glycols are well known articles of commerce which have been put to a variety of applications. For instance, the PEGs are used as plasticizers in other polymeric systems, the high molecular weight PEGs as hydrophilic excipients in compressed tablets for oral drug delivery, and within osmotic minipumps. They are commonly used at low concentrations as dispersing agents in aqueous suspensions and as cosolvents with water or ethanol. For instance, U.S. Pat. No. 4,041,155 discloses a composition of an aqueous formulation of 80% PEG 400 and somatostatin which reportedly sustained release of the active agent for 4 hours. Finally, European Patent Application 0 140 255 discloses a sustained release composition of interferon and a biodegradable carrier which is dispersed in a viscous solvent, e.g. polyethylene glycol. To my knowledge, there are no published reports of the use of a polyethylene glycol suspension for sustained release of a bioactive protein.

Polyethylene glycols ($\alpha$-hydro-$\omega$-hydroxypoly(oxy-1,2-ethanediyl) have the general formula $H(OCH_2CH_2)_nOH$ where $n \geq 4$ and are included in the GRAS (generally regarded as safe) list compiled by the U.S. Food and Drug Administration.

The ease and rapidity which somatotropin and growth hormone releasing factor are suspended either in triacetin and in polyethylene glycol is entirely unexpected in view of the failure of numerous non-aqueous, water-miscible solvents as suspension vehicles. I have found that these non-aqueous, water-miscible organic solvents provide unexpectedly and surprisingly prolonged release of proteins suspended therein.

INFORMATION DISCLOSURE

U.S. Pat. Nos. 3,966,962, 4,301,175, and 4,680,312 disclose solutions of prostaglandin-like compounds in triacetin, in triacetin with ethanol, and in triacetin with colloidal silicon dioxide as stable and/or water miscible formulations.

The Merck Index, 11th Edition, reports triacetin is soluble in water to the extent of about one part triacetin to 14 parts water.

GB 1185340 reports the use of triacetin as a dispersing agent in the food industry for hydrophilic colloids, e.g. gelatin.

The Merck Index, 11th Edition, page 1204, lists a variety of uses for the PEGs, including, water-soluble lubricants, in food packaging, in hair and cosmetic preparations, and as an ointment and suppository base in pharmaceuticals.

U.S. Pat. No. 4,041,155 discloses a composition of an aqueous formulation of 80% PEG 400 and somatostatin which reportedly sustained release of the active agent for 4 hours.

European Patent Application 0 140 255 discloses a composition for sustained release comprising interferon and a biodegradable carrier dispersed in a viscous solvent, e.g. polyethylene glycol.

SUMMARY OF THE INVENTION

The present invention relates to compositions of proteins in triacetin or polyethylene glycol (PEG). More particularly, the invention provides prolonged release of hormones, most particularly growth hormone or somatotropin and growth hormone releasing factor.

A particular embodiment of this aspect of the invention provides bovine somatotropin suspended in triacetin in a concentration of about five to about fifty percent (W/V).

An alternative embodiment of this aspect of the invention provides bovine somatotropin suspended in PEG 400 in a concentration of about five to about fifty percent (w/v).

An additional aspect of the invention provides the use of the compositions of the invention as sustained release vehicles, especially for subcutaneous and intramuscular injection.

More particularly, this aspect of the invention relates to the use of somatotropin suspended in triacetin or polyethylene glycol 400 to increase milk production in cows.

Most particularly, this aspect of the invention relates to the use of the somatotropin suspended in triacetin or in PEG, in a concentration of about ten to about thirty percent for injection into cows to increase milk production.

DETAILED DESCRIPTION

Polyethylene glycols (α-hydro-ω-hydroxypoly(oxy-1,2-ethanediyl) have the general formula $H(OCH_2CH_2)_nOH$ where $n \geq 4$. PEGs are assigned a numerical suffix based on the average value of n and, thus, include polymers having a range of molecular weights. Using this system a polymer having an average value for n of 4 has a range of molecular weights of 190–210 is designated PEG 200; a polymer having an average range of values for n of 8.2–9.1 has a range of molecular weights of 380–420 and is designated PEG 400; a polymer having an average range of values for n of 12.5–13.9 has a range of molecular weights of 570–630 and is designated PEG 600. For a more detailed description, see The Merck Index, 11th Edition, page 1204.

The compositions of the invention are conveniently and easily made by dispersing or stirring the protein into the triacetin or polyethylene glycol (PEG). PEG compositions of the invention having values of $4 \leq n \leq 20$ are preferred. The compositions having the values of $6 \leq n \leq 10$, i.e., PEG 300 and PEG 400, are most preferred. The protein can be readily dispersed in the triacetin or PEG vehicle by mixing in a beaker or other suitable container until a homogenous dispersion is obtained. Alternatively, mixing may be effected by typical high-shear dispersion equipment. In addition, the compositions of the invention may be conveniently made and stored under aseptic conditions. The amount of protein to be added depends on, for example, the protein dose and volume to be administered, as well as by the viscosity, syringeability, and injectability of the final formulation. These and other factors are well known and adjustments easily made by a person skilled in the art of formulation technology.

Any protein or peptide the sustained or prolonged release of which is desired to be effectuated, is suitable for use in the compositions of the invention. Of particular interest are those proteins or peptides which are unstable under the aqueous conditions encountered upon administration and are bioactive upon release into the circulatory system. Preferred proteins or peptides for the incorporation into the compositions of the invention are insulin and insulin-like growth factors, interferon, growth hormone releasing factor, interleukins, etc. Most preferred are the growth hormones or somatotropins, especially bovine and porcine somatotropin, and growth hormone releasing factor. The protein or peptide may be obtained from the natural tissue ("native") or produced by recombinant technology ("recombinant") and includes proteins or peptides having modified or varied amino acid sequences. The essential feature is that the protein or peptide retain bioactivity in the species into which it is administered. The protein or peptide is to be added in a dry state, e.g., powder, cake, lyophilized, spray dried, granulated air dried, milled protein, etc., and with or without additives. Thus, it is preferred to obtain the protein or peptide in the appropriate physical state.

The compositions of the invention are used for the same purposes and by the same method as the prior art prolonged or sustained release protein compositions. Accordingly, dosage forms in accordance with the present invention are used for various purposes and dosage levels known in the art, e.g., for the prolonged release of bovine somatotropin by injection into bovine to effectuate increased milk yields and/or increases in lean tissue (U.S. Pat. Nos. 5,013,713, and 4,977,140), for the prolonged release of insulin, ACTH, glucagon (U.S. Pat. No. 2,902,408), LHRH (B. K. Davis, Experentia and Proc. Natl. Acad. Sci. (1972)), and cyclosporin (U.S. Pat. No. 4,388,307). Thus, the triacetin and PEG formulations of the invention are suitable for use in both human and non-human animals.

Upon administration, the compositions of the invention provide a slow release of the active agent, i.e., protein or peptide, from a depot formulation. This is surprising indeed, in view of the relatively rapid exposure of the protein depot to the destabilizing aqueous environment. Unlike prior art oleaginous suspensions, the present composition of the invention provide a water-miscible, non-aqueous vehicle which unexpectedly provides a redispersable suspension and, again unexpectedly, provides acceptably prolonged duration of release, while maintaining stability and ease of use similar to that of the prior art oil suspensions. The compositions of the invention may optionally include preservatives, gelling agents, dispersing agents, stabilizers, etc., known in the art to further optimize the prolonged release of the protein or peptide from the depot or to further enhance the stability of the formulation.

All chemicals used are reagent grade or better and are available from commercial vendors. Triacetin is obtained from Sigma Chemical Co. and can be sterilized using pharmaceutically acceptable methods, e.g., filtration, heat treatment, etc., prior to use. The various polyethylene glycols are widely available from commercial vendors. The PEGs also may be sterilized using pharmaceutically acceptable methods, e.g., filtration, heat treatment, etc., prior to use.

While the compositions of the invention and the use thereof are described here in some detail, one skilled in the art will appreciate that a variety of alterations in form and detail can be made without departing from the true scope of the invention.

Definitions

Certain terms and phrases used throughout the specification and claims have the following meanings:

"Bioactive" means a protein which has biological activity in the species of interest.

"W/V" means weight protein in grams per unit volume of suspension as administered.

EXAMPLES

The compositions of the present invention, and their use, may be more fully understood by the following examples.

These examples should in no way be construed to be limiting of the specification and claims. In the foregoing specification and examples which follow, the entire contents of all cited references are incorporated by reference.

Example 1
Somatotropin/Triacetin Sustained Release Formulation 25.01 g of triacetin is added to 6.85 grams of bioactive recombinant bovine somatotropin (Somavubove, The Upjohn Company) and mixed with a spatula to result with a suspension containing 200 mg rbSt/ml. The formulation is designated SR-SbV/TAC and is stored in a 20 ml stoppered vial until use.

Example 2
Serum Somatotropin (Triacetin)

Aliquots of the suspension made in Example 1 are removed for administration into non-pregnant non-lactating heifers. Fifteen non-pregnant, non-lactating Holstein heifers are housed in dry lots in southwestern Michigan. Alfalfa/grass hay and water are available ad libitum; heifers also receive 15 kg corn silage per head per day. Heifers are assigned randomly to the following groups: (1) Control (no injection); (2) 150 mg SR-SbV/TAC (150 mg rbSt in triacetin); and (3) 300 mg SR-SbV/TAC (300 mg rbSt in triacetin).

The formulations are injected subcutaneously over the rib, caudal to the left shoulder. Hair at injection site is clipped prior to injection. The formulation is easily injected with an 18 gauge X 2.5 cm needle. Injection volume is 0.7 ml for heifers receiving 150 mg rbSt in triacetin and 1.5 ml for heifers receiving 300 mg rbSt in triacetin.

Blood is collected from the tail vein for 7 days following injection. Injections are given at time zero (0) and samples collected at 0, 6, 12, 18, 24, 30, 36, 48, 60, 72, 84, 96, 120, and 144 hours. Blood is allowed to clot, centrifuged, and serum decanted and stored at $-20°$ until assay by radioimmunoassay following the procedure of G. D. Niswander, et al., Endocrinol. 84:1166 (1969).

Analysis of variance for repeated measures design with treatment and time as main effects is used. The mean squares for animal within treatment and error are used to calculate a least significant difference which is used to determine the blood sampling times that the serum bSt concentration remained elevated above mean control concentration during the 7-day post-injection sampling period (G. A. Milliken and D. E. Johnson, *Analysis of Messy Data*, (1984); Lifetime Learning Publications, Belmont Calif.). The principal measurement of interest is the length of time the somatotropin formulations are able to increase serum somatotropin concentration above mean control concentration. Levene's test is utilized to determine homogeneity of variance for all analyses of variance. Data with heterogeneous variance ($P<0.05$) are transformed using logarithm base$_{10}$. Comparisons are made among the least squares means using the PDIFF option of the general linear models procedure of the Statistical Analysis System (SAS User's Guide: Statistics, Version 6, Fourth Edition (1990); SAS Institute, Inc. Cary, N.C.).

The mean serum bSt concentrations over time are depicted in Table 1. Referring to Table 1, it is apparent that regardless of dose, the greatest quantity of bSt appeared in the serum between 12 and 30 h post injection and remains elevated for at least 84 hours.

Injection site tissue reaction was also recorded. Advantageously, the triacetin formulations of the invention show very little tissue site reaction.

Finally, stability studies show that the triacetin suspensions of the inventions provide sufficient stability of the bioactive protein as is necessary for an economically viable, commercial product.

Example 3
Somatotropin/PEG Sustained Release Formulation 21.8 g of PEG 400 (Sigma Chemical) is added to 6.00 grams of bioactive recombinant bovine somatotropin (rbSt) (Somavubove, The Upjohn Company) and mixed with a spatula to result with a suspension containing 200 mg rbSt/ml. The formulation is designated SR-SbV/PEG and is stored in a 20 ml stoppered vial until use.

Example 4
Serum Somatotropin (PEG)

Aliquots of the suspension made in Example 3 are removed for administration into non-pregnant non-lactating heifers. Fifteen non-pregnant, non-lactating Holstein heifers are housed in dry lots in southwestern Michigan. Alfalfa/grass hay and water are available ad libitum; heifers also receive 15 kg corn silage per head per day. Heifers are assigned randomly to the following groups: (1) Control (no injection); (2) 150 mg SR-SbV/PEG (150 mg rbSt in PEG 400); and (3) 300 mg SR-SbV/PEG (300 mg rbSt in PEG 400).

The formulations are injected subcutaneously over the rib, caudal to the left shoulder. Hair at injection site is clipped prior to injection. The formulation is easily injected with an 18 gauge X 2.5 cm needle. Injection volume is 0.7 ml for heifers receiving 150 mg rbSt in PEG 400 and 1.5 ml for heifers receiving 300 mg rbSt in PEG 400.

Blood is collected from the tail vein for 7 days following injection. Injections are given at time zero (0) and samples collected at 0, 6, 12, 18, 24, 30, 36, 48, 60, 72, 84, 96, 120, and 144 hours. Blood is allowed to clot, centrifuged, and serum decanted and stored at $-20°$ until assay by radioimmunoassay following the procedure of G. D. Niswander, et al., Endocrinol. 84:1166 (1969).

Analysis of variance for repeated measures design with treatment and time as main effects is used. The mean squares for animal within treatment and error are used to calculate a least significant difference which is used to determine the blood sampling times that the serum bSt concentration remained elevated above mean control concentration during the 7-day post-injection sampling period (G. A. Milliken and D. E. Johnson, *Analysis of Messy Data*, (1984); Lifetime Learning Publications, Belmont, Calif.). The principal measurement of interest is the length of time the somatotropin formulations are able to increase serum somatotropin concentration above mean control concentration. Levene's test is utilized to determine homogeneity of variance for all analyses of variance. Data with heterogeneous variance ($P<0.05$) are transformed using logarithm base$_{10}$. Comparisons are made among the least squares means using the PDIFF option of the general linear models procedure of the Statistical Analysis System (SAS User's Guide: Statistics, Version 6, Fourth Edition (1990); SAS Institute, Inc. Cary, N.C.).

The mean serum bSt concentrations over time are depicted in Table 2. Referring to Table 2, it is apparent that regardless of dose, the greatest quantity of bSt appeared in the serum between 12 and 30 h post injection and remains elevated for at least 72 hours (150 mg) and 84 hours (300 mg).

Finally, stability studies show that the PEG 400 suspension of the invention provides sufficient stability of the bioactive protein as is necessary for an economically viable, commercial product.

Example 5
GRF/Triacetin Sustained Release Formulation 10.3 milligrams of a bioactive lyophilized analog of bovine growth releasing factor was weighed out and suspended in 0.5 ml of triacetin by gentle shaking to yield a dispersible suspension containing about 20.6 mg GRF/ml. The formulation is designated SR-GRF/TAC and is stored in a glass vial. Stability studies show that the triacetin/GRF suspension was easily redispersed following storage at room temperature for 10 days.

Example 6
GRF/PEG Sustained Release Formulation 10.3 milligrams of a bioactive lyophilized analog of bovine growth releasing factor was weighed out and suspended in 0.5 ml of PEG 400 (Sigma Chemical) by gentle shaking to yield a dispersible suspension containing about 20.6 mg GRF/ml. The formulation is designated SR-GRF/PEG and is stored in a glass vial. Stability studies show that the PEG 400/GRF suspension was easily redispersed following storage at room temperature for 10 days.

TABLE 1

Serum bSt Concentration in Heifers by Bleeding Times After Injection of SR-SbV/TAC

| Time | 150 mg SR-SbV/TAC | 300 mg SR-SbV/TAC |
|---|---|---|
| 6 h | 44.6 | 68.8 |
| 12 h | 53.1 | 103.5 |
| 18 h | 46.0 | 115.2 |
| 24 h | 41.6 | 115.5 |
| 30 h | 49.2 | 127.0 |
| 36 h | 37.6 | 114.9 |
| 48 h | 22.6 | 65.9 |
| 60 h | 15.7 | 39.4 |
| 72 h | 11.8 | 15.7 |
| 84 h | 8.3 | 11.2 |
| 96 h | $4.8^{ns}$ | $5.1^{ns}$ |
| 120 h | $4.4^{ns}$ | 4.9 |
| 144 h | $4.9^{ns}$ | $3.2^{ns}$ |

$^a$least squares means (ng bSt/ml of serum).
$^{ns}$Means with this superscript are not significantly (P > .05) different from overall control mean (3.7 ng bSt/ml serum). The control mean is the average concentration of bSt for all blood sampling times (through 144 h).

TABLE 2

Serum bSt Concentration in Heifers by Bleeding Times After Injection of SR-SbV/PEG

| Time | 150 mg SR-SbV/PEG | 300 mg SR-SbV/PEG |
|---|---|---|
| 6 h | 31.9 | 59.0 |
| 12 h | 42.7 | 85.3 |
| 18 h | 43.9 | 79.4 |
| 24 h | 31.2 | 66.0 |
| 30 h | 31.5 | 72.9 |
| 36 h | 21.1 | 50.9 |
| 48 h | 12.3 | 28.1 |
| 60 h | 6.7 | 19.4 |
| 72 h | $3.9^{ns}$ | 10.7 |
| 84 h | $3.0^{ns}$ | 7.5 |
| 96 h | $2.1^{ns}$ | $3.2^{ns}$ |
| 120 h | $2.4^{ns}$ | $2.3^{ns}$ |
| 144 h | $3.2^{ns}$ | $1.8^{ns}$ |

$^a$least squares means (ng bSt/ml of serum).
$^{ns}$Means with this superscript are not significantly (P > .05) different from overall control mean (3.7 ng bSt/ml serum). The control mean is the average concentration of bSt for all blood sampling times (through 144 h).

I claim:

1. A nonaqueous composition consisting essentially of a therapeutically effective amount of a bioactive protein suspended in polyethylene glycol wherein said bioactive protein is selected from the group consisting of somatotropin and growth hormone releasing factor and said polyethylene glycol is selected from the group consisting of PEG 300 to PEG 600.

2. A composition of claim 1 wherein the polyethylene glycol is PEG 300.

3. A composition of claim 2 wherein the bioactive protein is porcine somatotropin.

4. A composition of claim 2 wherein the bioactive protein is bovine somatotropin.

5. A composition of claim 2 wherein the bioactive protein is growth hormone releasing factor.

6. A composition of claim 4 wherein the bovine somatotropin concentration is about five to about fifty percent (W/V).

7. A composition of claim 6 wherein the bovine somatotropin concentration is about ten to about thirty percent (W/V).

8. A composition of claim 1 wherein the polyethylene glycol is PEG 400.

9. A composition of claim 8 wherein the bioactive protein is porcine somatotropin.

10. A composition of claim 8 wherein the bioactive protein is bovine somatotropin.

11. A composition of claim 8 wherein the bioactive protein is growth hormone releasing factor.

12. A composition of claim 10 wherein the bovine somatotropin concentration is about five to about fifty percent (W/V).

13. A composition of claim 12 wherein the bovine somatotropin concentration is about ten to about fifty percent (W/V).

14. A nonaqueous composition consisting essentially of a therapeutically effective amount of a bioactive protein suspended in polyethylene glycol wherein said polyethylene glycol is PEG 200 and said bioactive protein is selected from the group consisting of bovine somatotropin and growth hormone releasing factor.

15. A composition of claim 14 wherein the bioactive protein is bovine somatotropin.

16. A composition of claim 14 wherein the bioactive protein is growth hormone releasing factor.

17. A composition of claim 15 wherein the bovine somatotropin concentration is about five to about fifty percent (W/V).

18. A composition of claim 17 wherein the concentration is about ten to about thirty percent (W/V).

19. A method of achieving prolonged release of a bioactive protein comprising subcutaneous or intramuscular injection of a non-aqueous composition consisting essentially of a therapeutically effective amount of a bioactive protein suspended in polyethylene glycol wherein said bioactive protein is selected from the group consisting of somatotropin and growth hormone releasing factor and said polyethylene glycol is selected from the group consisting of PEG 300 to PEG 600.

20. The method of claim 19 wherein the polyethylene glycol is PEG 300.

21. The method of claim 20 wherein the bioactive protein is porcine somatotropin.

22. The method of claim 20 wherein the bioactive is protein is bovine somatotropin.

23. The method of claim 20 wherein the bioactive protein is growth hormone releasing factor.

24. The method of claim 22 wherein the bovine somatotropin concentration is about five to about fifty percent.

25. The method of claim 24 wherein the bovine somatotropin concentration is about ten to about thirty percent.

26. The method of claim 19 wherein the polyethylene glycol is PEG 400.

27. The method of claim 26 wherein the bioactive protein is porcine somatotropin.

28. The method of claim 26 wherein the bioactive protein is bovine somatotropin.

29. The method of claim 26 wherein the bioactive protein is growth hormone releasing factor.

30. The method of claim 28 wherein the bovine somatotropin concentration is about five to about fifty percent.

31. The method of claim 30 wherein the bovine somatotropin concentration is about ten to about fifty percent.

32. A method of achieving prolonged release of a bioactive protein comprising subcutaneous or intramuscular injection of a non-aqueous composition consisting essentially of a therapeutically effective amount of a bioactive protein suspended in polyethylene glycol where said polyethylene glycol is PEG 200 and said bioactive protein is selected from the group consisting of bovine somatotropin and growth hormone releasing factor.

33. The method of claim 32 wherein the bioactive protein is bovine somatotropin.

34. The method of claim 32 wherein the bioactive protein is growth hormone releasing factor.

35. The method of claim 33 wherein the bovine somatotropin concentration is about five to about fifty percent.

36. The method of claim 35 wherein the concentration is about ten to thirty percent.

* * * * *